United States Patent [19]
Warden

[11] Patent Number: 5,170,420
[45] Date of Patent: Dec. 8, 1992

[54] RADIOLOGICAL APPARATUS FOR MAMMOGRAPHIC EXAMINATIONS

[75] Inventor: Hans-Erik Warden, Upplands Vaesby, Sweden

[73] Assignee: Siemens Aktiengesellschaft, Munich, Fed. Rep. of Germany

[21] Appl. No.: 828,129

[22] Filed: Jan. 30, 1992

[30] Foreign Application Priority Data

Feb. 5, 1991 [SE] Sweden ............................... 9100362

[51] Int. Cl.⁵ .............................................. A61B 6/04
[52] U.S. Cl. ...................................... 378/37; 378/196; 378/197
[58] Field of Search ................... 378/37, 195, 196, 197

[56] References Cited

U.S. PATENT DOCUMENTS 4,613,982  9/1966  Dornheim et al. .
5,050,197  9/1991  Virta et al. ............................. 378/37

FOREIGN PATENT DOCUMENTS

WO89/11248  11/1989  PCT Int'l Appl. .

Primary Examiner—Craig E. Church

[57] ABSTRACT

A mammography apparatus has a holder for a radiation source, the holder being rotatable around a horizontal axle which extends from a bearing which is vertically displaceable in a stand. The holder is maintained at a selected height by a weight compensation system operating on the bearing. In order to permit the holder to be rotated while still maintaining the same vertical position from one exposure to another, so that the examination subject need not be re-positioned between exposures, the horizontal axle is disposed outside of the center of gravity of the holder, and is connected to a first part which extends parallel to the axle at a distance from the center line thereof. The first part engages a second part which is movable in the vertical direction, and is connected to the weight compensation system. The distance between the first part and the center line of the axle is selected to that, when the axle is rotated, the first part is displaced along a circular arc, and the second part is simultaneously vertically displaced so that the weight compensation system generates a force which balances the torque of the holder.

10 Claims, 2 Drawing Sheets

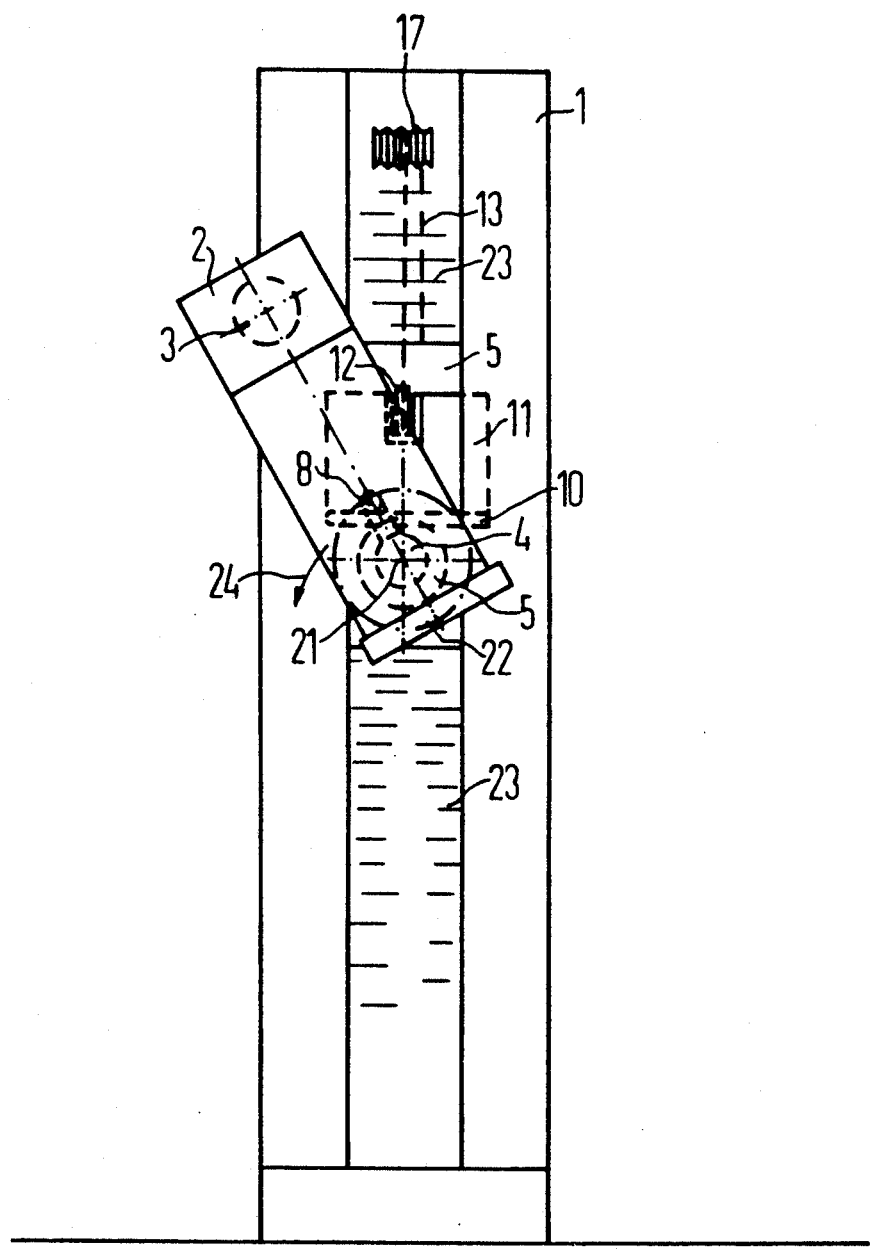

RADIOLOGICAL APPARATUS FOR MAMMOGRAPHIC EXAMINATIONS

FIELD OF THE INVENTION

The present invention is directed to a radiological apparatus for mammographic examinations, of the type having a holder for a radiation source, the holder being rotatable around a horizontal axle extending from a bearing, with the bearing being vertically displaceable in a stand, the holder being maintained at a selected height by a weight compensation system acting on the bearing.

DESCRIPTION OF THE PRIOR ART

A radiological examination apparatus for mammography is described in Siemens brochure "Mammomat 2" dated November, 1987. In this x-ray apparatus for mammographic examinations, the holder for an x-ray tube is rotatable around a horizontal axle, the axle being arranged in the center of gravity of the holder. The rotation of the holder around this axle ensues by means of a conventional spur gear. Vertical displacement of the holder ensues by means of a motor and a toothed rack, which are disposed separated from the spur gear of the holder.

For undertaking an x-ray examination of a breast, a first vertical exposure is undertaken, followed by a second exposure at an angle departing from the vertical in a range of from 45° through 60°. During the course of rotation of the holder from the first exposure position to the second exposure position, the height of the holder must be readjusted. Moreover, the patient must step aside, because rotation of the holder takes place outside the center axis of the examination subject.

SUMMARY OF THE INVENTION

It is an object of the present invention to provide a radiological mammography apparatus of the type described above wherein the movements of the holder can be accomplished by a relatively simple structure, and wherein the holder can be turned so that the holder retains its vertical position from one exposure to another, at arbitrary angles, while permitting the patient to remain standing at the same location.

The above objects are achieved in accordance with the principles of the present invention in a radiological mammography apparatus wherein the axle for the holder is disposed outside the center of gravity of the holder, and is connected to a first part which is disposed parallel to the axle and spaced from the center line of the axle. The first part engages a second part which is movable in the vertical direction, and is connected to a weight compensation system. The distance between the first part and the center line of the axle is selected so that, when turning the axle, the first part is displaced along a circular arc and the second part is vertically displaced by the weight compensation system generating a force which balances the torque of the holder. The same weight compensation system is used for vertical displacement of the holder and the rotation thereof around its horizontal axle, the axle in the mammography apparatus disclosed herein approximately coinciding with the middle of the examination subject. This means that neither the holder nor the patient need be re-positioned given a change in the exposure angle.

In a further embodiment of the invention, the second part is controllable in the vertical direction. A stable, vertical motion is obtained in this manner.

In another embodiment of the invention, the second part is provided with a horizontal slot in which the first part is displaceable. A reliable connection between the two parts is established in this manner. Additionally, the second part may be provided with a horizonal ledge having a surface on which the first part rides.

In a structurally simple embodiment of the invention, the first part is provided with a running roller. This permits the first part to ride easily in the slot or on the ledge.

Further, the second part may be provided with a roller around which a cable proceeds, with one end of the cable being connected to the bearing for the aforementioned horizontal axle, and the second end of the cable being connected to the weight compensation system. A translation of the equilibrium force is thereby obtained such that only a relatively short distance is necessary between the center line of the axle and the free end of a crank-shaped part which is secured to the end of the axle which carries the running roller. The space requirement is reduced in this embodiment.

DESCRIPTION OF THE DRAWINGS

FIG. 2 is a front elevational view of the radiological examination apparatus of FIG. 1.

DESCRIPTION OF THE PREFERRED EMBODIMENTS

Figure 1:
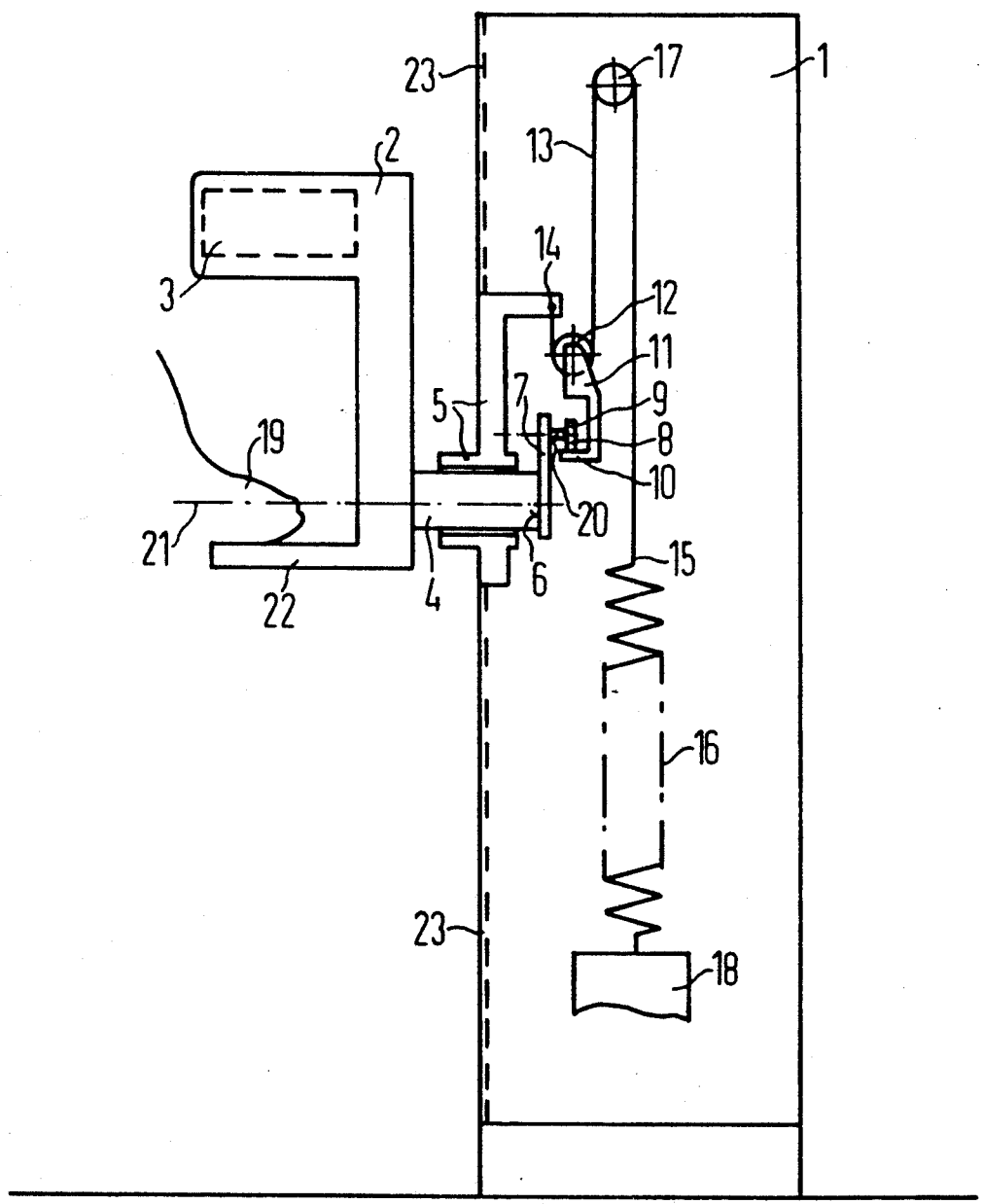
FIG. 1 is a side elevational view of a radiological examination apparatus constructed in accordance with the principles of the present invention.

The basic components of an x-ray apparatus for mammographic examinations constructed in accordance with the principles of the present invention is shown in FIG. 1. The apparatus includes a stand 1 and a holder 2, which carries an x-ray tube 3. The holder 2 is rotatably connected to a bearing 5 via a horizontal axle 4. The bearing 5 is arranged in the stand 1 so as to be displaceable in the vertical direction. A free end 6 of the axle 4 is connected to a crank-shaped part 7, which has a free end 20 pointing away from the axle 4. The free end 20 is arranged parallel to the axle 4 at a distance from the center line 21 of the axle 4. A running roller 8 is attached to the free end 20 of the crank-shaped part 7, the running surface 9 (perimeter) of the roller 8 pressing against a horizontal surface formed by a ledge 10 extending from a moment-balancing carriage 11.

The carriage 11 is displaceable in the vertical direction, and is provided with a roller 12 around which a cable 13 proceeds. One end 14 of the cable 13 is connected to the bearing 5 and the other end 15 of the cable 13 is connected to a weight compensation system. In the exemplary embodiment of FIG. 1, the weight compensation system is formed by an equilibrium drum 17 and a tension spring 16 which is secured to the stand 1 at a fastening point 18. The equilibrium drum 17 operates so that the force of equilibrium is constant independently of the position of the tension spring 16. The roller 12 forms a pulley block by means of which the equilibrium force is transmitted. The moment-balancing carriage 11 may have a slot instead of the ledge 10, the free end of the crank-shaped part 7, or the running roller 8, being displaceable in this slot.

As can be seen in both FIGS. 1 and 2, louver-like coverings 23 are secured to the bearing 5, which close the vertical opening in the stand 1 in which the bearing 5 moves. The coverings 23 prevent dust from penetrating into the stand 1.

In a routine examination of a breast 19 of a patient, the holder 2, and a specimen stage secured to the holder 2, are displaced to a vertical position which is matched to the physical height of the patient. The holder 2 with the axle 4 and the bearing 5 is displaced upwardly or downwardly, with the carriage 11 following this motion due to the cable 13. The holder 2 is balanced in every position due to the weight compensation system. The breast 19 is then placed on the specimen stage 22 in order, as shown in FIG. 1, to make a vertical exposure. The holder 2 is then turned by an angle of from 45° through 60° for a further mammographic exposure. Such a position of the holder 2 is shown in FIG. 2. When the holder 2 is turned around its axle 4, the crank-shaped part 7 is also turned, causing the running roller 8 to be forced against the ledge 10, so that the ledge 10 and the carriage 11 are pressed downwardly. As a result of the operation of the same weight compensation system which balances the weight of the holder 2, a force is produced which compensates the torque of the holder 2, so that the holder 2 remains in the described position as a result. Typically, the physician will conduct a more precise follow-up examination, in which the physician will select exposure angles in addition to those already set forth. For example, the holder 2 can be turned in either direction of the arrow 24, as a result of which the carriage 11 is downwardly displaced by the running roller 8 pressing against the ledge 10. The holder 2 can thus be turned around the axle 4 through 360°, and will be balanced in any arbitrary angular position, so that any arbitrary exposure angle can be set.

As a result of the structure of the radiological examination apparatus disclosed herein, the axle 4 for the holder 2 can be disposed outside of the center of gravity of the holder 2. By displacing the axle 4, i.e., the pivot point of the holder 2, to approximately the center of the examination subject 19, it is not necessary to adjust the holder 2 in height when changing the exposure angle. Moreover, the patient can remain standing when the exposure angle is changed, thereby saving significant time.

Although modifications and changes may be suggested by those skilled in the art, it is the intention of the inventor to embody within the patent warranted hereon all changes and modifications as reasonably and properly come within the scope of his contribution to the art.

I claim as my invention:

1. A radiological apparatus for mammography examinations comprising:
   a holder with an x-ray means mounted thereon for making a mammography exposure;
   an axle about which said holder is rotatable, said axle having a center line and being disposed outside the center of gravity of said holder;
   a first part connected to said axle extending parallel to and spaced from said center line of said axle;
   a second part engaging said first part and being vertically movable; and
   means connected to said second part for compensating the weight of said holder and for, in combination with the spacing between said first part and said center line, generating a force for compensating the torque of said holder by vertically displacing said second part when said holder is rotated in a circular arc around said axle.

2. A radiological apparatus as claimed in claim 1 further comprising means for controlling the height of said second part in the vertical direction.

3. A radiological apparatus as claimed in claim 1 wherein said second part has a horizontal slot in which a free end of said first part is displaceably disposed.

4. A radiological apparatus as claimed in claim 3 wherein said free end of said first part has a roller which runs in said slot.

5. A radiological apparatus as claimed in claim 1 wherein said second part has a horizontal surface formed by a ledge on which a free end of said part runs.

6. A radiological apparatus as claimed in claim 5 wherein said free end of said first part has a roller which runs on said horizontal surface.

7. A radiological apparatus as claimed in claim 1 further comprising:
   a bearing in which said axle of said holder is rotatably disposed;
   a roller attached to said second part; and
   a cable proceeding around said roller and having one end connected to said bearing and an opposite end connected to said means for compensating for the weight of said holder.

8. A radiological apparatus as claimed in claim 7 wherein said roller and said second part form a pulley block.

9. A radiological apparatus as claimed in claim 1 wherein said holder has a rotational center substantially coinciding with a center of an examination subject.

10. A radiological apparatus as claimed in claim 1 wherein said holder has a specimen table.

* * * * *